United States Patent
Vanney

(12) 
(10) Patent No.: US 6,193,726 B1
(45) Date of Patent: Feb. 27, 2001

(54) INSERTION TOOL FOR TRANSMYOCARDIAL IMPLANT

(75) Inventor: Guy P. Vanney, Blaine, MN (US)

(73) Assignee: Heartstent Corporation, St. Paul, MN (US)

( * ) Notice: Subject to any disclaimer, the term of this patent is extended or adjusted under 35 U.S.C. 154(b) by 0 days.

(21) Appl. No.: 09/232,272

(22) Filed: Jan. 15, 1999

(51) Int. Cl.$^7$ ........................................ A61F 11/00
(52) U.S. Cl. .................. 606/108; 606/99; 606/194; 604/164; 623/1.11
(58) Field of Search .................. 604/53, 8, 164; 623/1.1, 1.2, 1.13, 1.11; 606/194, 108, 99

(56) References Cited

U.S. PATENT DOCUMENTS 5,755,682 5/1998 Knudson et al. .

FOREIGN PATENT DOCUMENTS

WO 98/06356 2/1998 (WO) .

OTHER PUBLICATIONS

Product Brochure, "Ordering Information", *Medcomp*, CAT–014. PM5 (May 1997).
U.S. Application No. 08/822,397, filed Jun. 25, 1997.
U.S. Application No. 08/944,313, filed Oct. 6, 1997.
U.S. Application No. 09/063,160, filed Apr. 20, 1998.

*Primary Examiner*—Michael Buiz
*Assistant Examiner*—Anthony S. King
(74) *Attorney, Agent, or Firm*—Merchant & Gould P.C.

(57) ABSTRACT

An insertion tool facilitates insertion of a vessel end of a transmyocardial implant into a coronary vessel. The insertion tool has a hollow sheath and mating dilator. The sheath has an external dimension sized for the sheath to be received within a lumen of an expanded size of the coronary vessel. A tapered portion extends from the dilator coaxially with an axis of the sheath. The tapered portion narrows from a cylindrical body portion to a leading tip of the tapered portion. The leading tip of the tapered portion is sized to be received within the lumen of a constricted size of the coronary vessel. The tapered portion and body portion are retractable from the sheath. After such retraction, the leading end of the implant is placed within the sheath. The sheath is split at a part-line such that the sheath can be pulled rearwardly from the vessel without disrupting the coronary vessel following placement of the implant within the sheath.

4 Claims, 3 Drawing Sheets

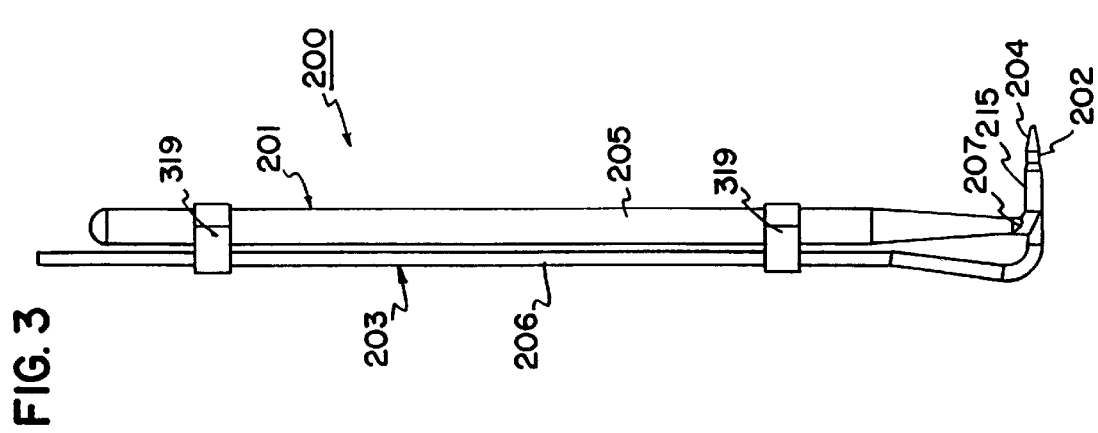

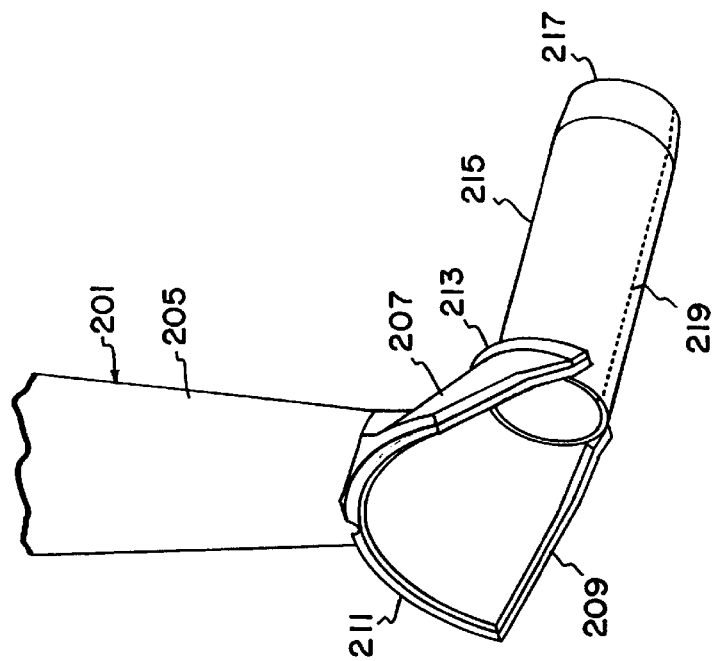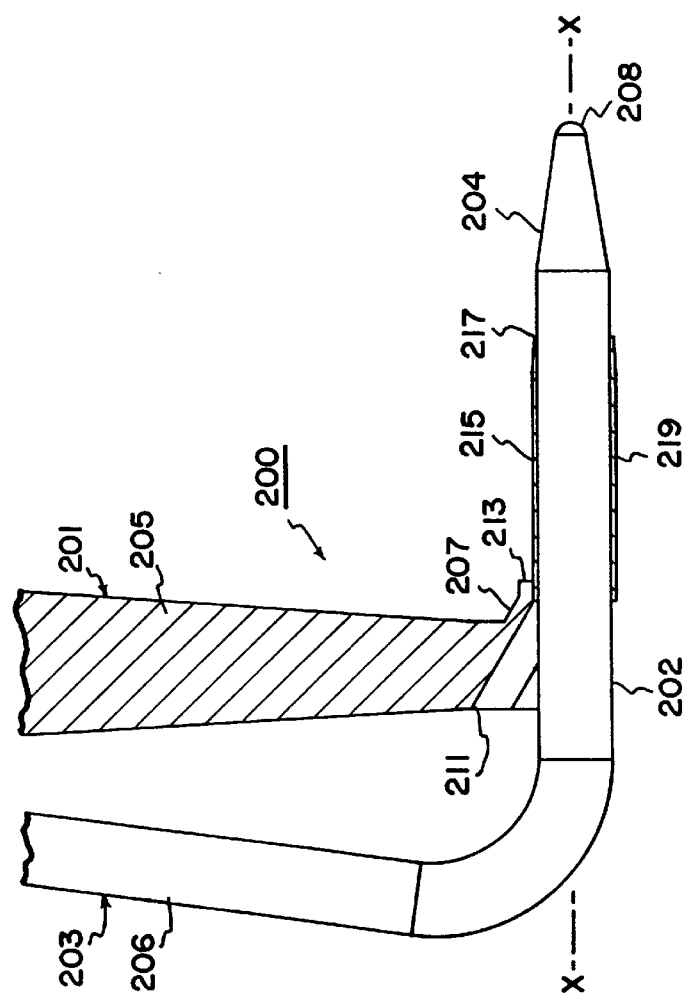

US 6,193,726 B1

INSERTION TOOL FOR TRANSMYOCARDIAL IMPLANT

BACKGROUND OF THE INVENTION

1. Field of the Invention

This invention pertains to an implant for passing blood flow directly between a chamber of the heart and a coronary vessel. More particularly, this invention pertains to an insertion tool to facilitate insertion of such an implant into the coronary vessel.

2. Description of the Prior Art

U.S. Pat. No. 5,755,682 dated May 26, 1998 and PCT Application No. PCT/US97/13980 (International Publication No. WO 98/06356 based U.S. patent application Ser. No. 08/882,397 filed Jun. 25, 1997) teach an implant for defining a blood flow conduit directly from a chamber of the heart to a lumen of a coronary vessel. An embodiment disclosed in the aforementioned patent and applications teaches an L-shaped implant in the form of a rigid conduit. The conduit has one leg sized to be received within a lumen of a coronary artery and a second leg sized to pass through the myocardium and extend into the left ventricle of the heart. As disclosed in the above-referenced patent and applications, the conduit is rigid and remains open for blood flow to pass through the conduit during both systole and diastole. The conduit penetrates into the left ventricle in order to prevent tissue growth and occlusions over an opening of the conduit.

Commonly assigned and co-pending U.S. patent application Ser. No. 08/944,313 filed Oct. 6, 1997, entitled "Transmyocardial Implant" teaches an implant such as that shown in the aforementioned '682 patent with an enhanced fixation structure. The enhanced fixation structure includes a fabric surrounding at least a portion of the conduit to facilitate tissue growth on the exterior of the implant.

Implants such as those shown in the aforementioned applications include a portion to be placed within a coronary vessel and a portion to be placed within the myocardium. When placing a portion of the implant in the coronary vessel, the vessel is axially incised a length sufficient to insert the implant. Such an incision results in a contraction of the coronary vessel to a size substantially smaller than the implant. Therefore, it is difficult to insert the implant into the lumen of the coronary vessel. Such vessels are elastic and can be urged to an expanded shape sufficient to fit over the implant. However, due to the small size of the vessel, restricted space for manipulating surgical tools, and the importance of avoiding damage to the coronary vessel, such a manipulation of the vessel is difficult.

SUMMARY OF THE INVENTION

According to a preferred embodiment of the present invention, an insertion tool is disclosed for facilitating insertion of a vessel end of a transmyocardial implant into a coronary vessel. The transmyocardial implant has a hollow conduit for establishing a blood flow path through a myocardium between a heart chamber and a lumen of a coronary vasculature residing on an exterior of said wall. The vessel end has an external geometry for the vessel end to be received within the lumen. The vessel end has a generally tubular external geometry and an axial opening at a leading end. The coronary vessel has a constricted size and is expandable to a larger expanded size. The insertion tool includes a sheath having an external dimension sized for the sheath to be received within the lumen of the expanded size of the coronary vessel. A dilator is removably inserted through the sheath. A leading end of the dilator is sized to be received within the lumen of the constricted size of the coronary vessel. The dilator is removed from the sheath after placement of the dilator and sheath in the vessel. The implant is then placed in the sheath. The sheath is retracted from the vessel without disrupting the coronary vessel.

BRIEF DESCRIPTION OF THE DRAWINGS

FIG. 3 is a side-elevation view of an insertion tool according to the present invention;

FIG. 4 is the view of FIG. 3 and showing dilator and sheath components separated;

FIG. 5 is an enlarged view of the dilator inserted within the sheath and showing the sheath in cross-section; and FIG. 6 is a rear, bottom and side perspective view of the sheath.

DESCRIPTION OF THE PREFERRED EMBODIMENT

Figure 1:
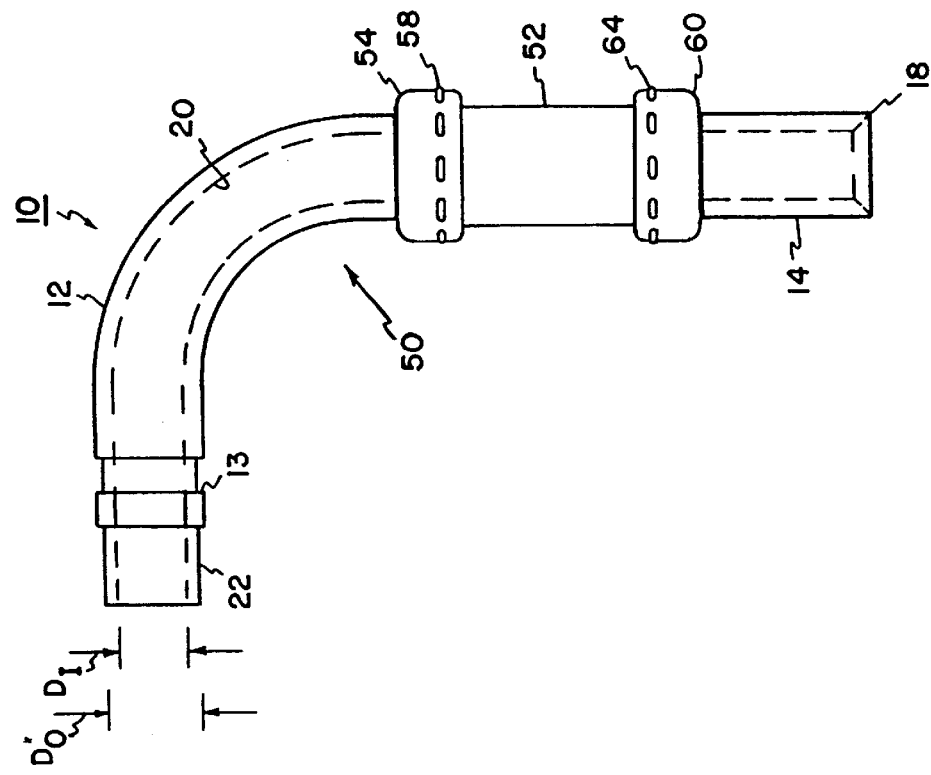
FIG. 1 is a side elevation view of an implant for use with the present invention.

With initial reference to FIG. 1, a conduit 10 is shown in the form of an L-shaped rigid tube. The conduit 10 may be formed of titanium or other rigid biocompatible material such as pyrolytic carbon or may be titanium coated with pyrolytic carbon. The material of the conduit 10 is preferably a rigid material in order to withstand contraction forces of the myocardium. By way of example, the tube will have an outside diameter $D_o$ of about 3.0–2.0 millimeters and an internal diameter $D_I$ of about 2.5–1.5 millimeters to provide a wall thickness of about 0.5 millimeters.

Figure 2:
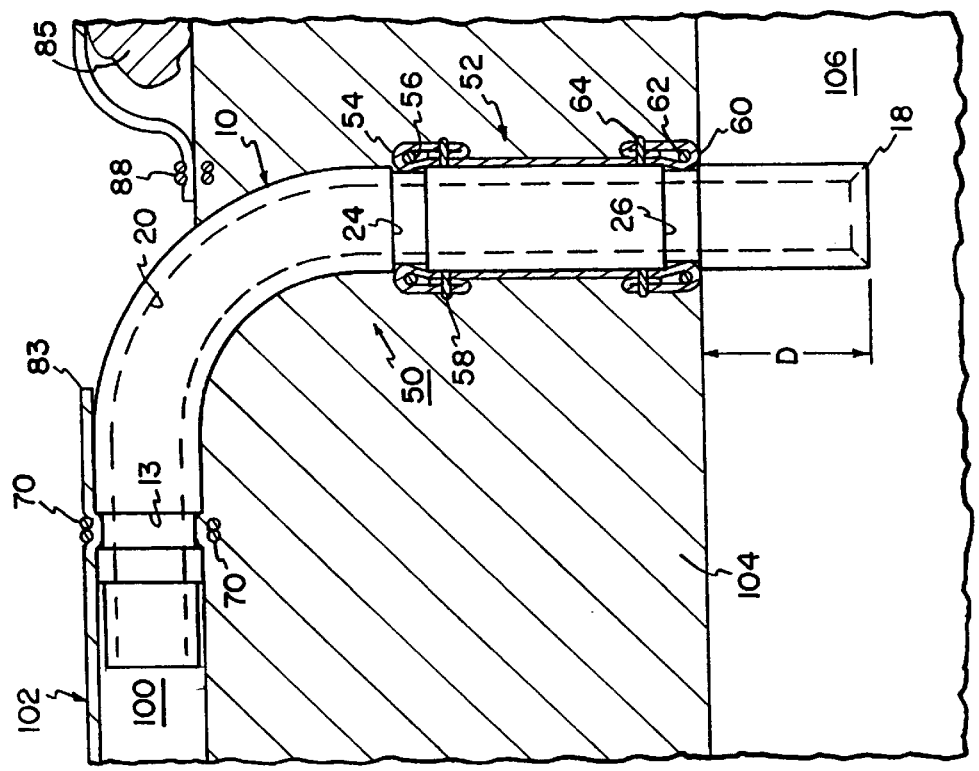
FIG. 2 is the view of FIG. 1 showing the implant of FIG. 1 and showing, in cross section, a tissue growth-inducing material secured to an exterior of the conduit and showing the implant positioned within the myocardium and lumen of a coronary vessel.

The tube 10 has a first portion (or vessel end) 12 sized to be received within the lumen of a coronary vessel such as the lumen 100 of a coronary artery 102 illustrated in FIG. 2. The conduit 10 has a second portion (or myocardium end) 14 extending at a right angle to the axis of portion 12. The second portion 14 is sized to extend from the coronary artery 102 directly through the myocardium 104 and protrude into the left ventricle 106 of a patient's heart. The second portion 14 is sized to have a length sufficient for the portion 14 to protrude into the left ventricle 106.

The vessel end 12 has a first opening 16 and the myocardium end 14 has a second opening 18 in communication with an interior 20 of the implant 10. Therefore, blood can freely flow through the implant 10 between the left ventricle 106 and the lumen 100 of the coronary artery 102. A leading end 22 of the vessel end 12 is tubular.

As illustrated in FIGS. 1 and 2, grooves 24, 26 are formed spaced-apart on the myocardium end 14. A sleeve 52 includes a first end 54 with sutures 56 disposed around end 54 to retain end 54 within the groove 24. The material at the first end 54 is folded over the sutures 56 and stitched by stitching 58 to secure the first end 54 in the groove 24 and to immobilize the first end 54 relative to the tube 10. Similarly, a second end 60 of the sleeve 52 is retained by sutures 62 in the groove 26 and threading 64 secures the material of the sleeve 52 over the sutures 62. In the figures, the stitching 58,64 is shown exposed on an exterior of the sleeve 52. Alternatively, the sleeve 52 can be formed inverted so that the stitching 58,64 is not exposed.

Preferably, the sleeve 52 is formed of a fabric having biocompatible fibers defining interstitial spaces to receive tissue growth. An example of such a fabric is polyethylene terephthalate (such as polyester fabric sold by DuPont Company under the trademark Dacron). Such a fabric permits rapid tissue integration into the fabric to anchor the fabric and, hence, the tube 10 to the patient's tissue. Additionally, the first portion 12 is secured in place by means of a reduced-diameter groove 13 formed adjacent the leading end 22. With the reduced-diameter groove 13, a surgeon can place sutures 70 surrounding the coronary artery 102 to secure the coronary artery 102 immobilized at the groove 13.

The foregoing description with reference to FIGS. 1 and 2 is provided for illustration and is more thoroughly described in the aforementioned U.S. patent application Ser. No. 08/944,313 entitled "Transmyocardial Implant".

In one method of placing the vessel end 12 into the artery 102, an incision 83 is made on an upper surface of the artery 102 distal to a coronary obstruction 85. The portion of the artery 82 proximal to the implant 10 is closed by sutures 88.

The process of incising the artery 102 results in contraction of the artery 102 to a reduced diameter. For example, an artery 102 such as the left anterior descending artery (LAD) may contract down to 0.5 mm. This is smaller than the diameter of the leading end 22 of the implant 10. The artery 102 is elastic and may be expanded to an enlarged expanded diameter (eg., 2–5 mm). However, it is difficult to manipulate tools to expand the artery 102 due to the small space available to work.

To facilitate placement of the implant 10 within the vessel 102, a novel insertion tool 200 is disclosed. The insertion tool 200 includes a sheath 201 and a mating dilator 203.

The sheath 201 includes a straight handle 205. A sheath funnel 207 is secured to an end of the handle with a funnel axis X—X perpendicular to the handle 205. A bottom side 209 of the funnel 207 is cut-away. The funnel 207 tapers from a large diameter trailing end 211 to a narrow leading end 213. The inner diameter of the trailing end 211 is larger than the outside diameter of the implant's leading end 22. The inside diameter of the leading end 213 is the same or only slightly larger than the outside diameter of the implant's leading end 22. By way of non-limiting example, for an implant 10 having an outside diameter $D_o$ of 2.5 mm, the inside diameter of the funnel training end 211 is 5.5 mm and the inside diameter of the of the funnel leading end 213 is 2.5 mm.

A hollow, cylindrical sheath body 215 is secured to the leading end 213 of the funnel 207. The cylindrical axis of the sheath body 215 is co-linear with axis X—X. In the foregoing example, the sheath body will have a substantially uniform inside diameter of 2.5 mm and, except as will be described, an outside diameter of 2.7 mm. At its leading end 217, the outside diameter of the sheath body 215 is tapered down to 2.5 mm. Preferably, the leading end 215 is rounded so as not to present a sharp edge to a coronary vessel upon insertion.

On a side of the sheath body 215 opposite handle 205, the sheath body 215 is scored by a score line 219 running axially the entire length of the sheath body 215. The score line 219 may be a partial cut through the material of the sheath body 215 to weaken the material such that upon application of force, as will be described, the sheath body 215 will tear along the score line 219. Alternatively, the score line 219 can be a lengthwise through-cut (as shown in the drawings) or can be a series of holes to define a perforation line.

The dilator 203 has cylindrical body portion 202 and a conical, tapered portion 204. The tapered portion 204 extends axially from the body portion 202. The opposite end of the body portion 202 is provided with a handle 206 to permit grasping of the dilator 206. The handle 206 projects at a 90° angle to the axis of the body portion 202.

The dilator body portion 202 is sized with an outside diameter the same or slightly larger than the inside diameter of the sheath body 215. In the example given, the body portion has an outside diameter of 2.5 mm. The tapered portion tapers to a rounded leading end 208 which, in the example given, has a diameter of 1.0 mm.

The dilator 203 is secured to the sheath 201 by the dilator handle 206 being releasably secured in clips 319 on the sheath handle 205. With the dilator 203 so secured to the sheath 201, the dilator body portion 202 is slidably received within the sheath body 215 and the dilator tapered portion 204 protrudes beyond the sheath leading end 217.

The leading end 208 of the tapered portion 204 is sized to have a diameter sufficiently small for the leading end 208 to slip into the lumen 100 of the contracted size artery 102. Further advancement of the dilator and sheath dilates the vessel. A small portion of the full diameter dilator body 202 extends beyond the sheath leading end 217 so the vessel is fully dilated before the sheath body 215 is urged into the vessel.

The contracted size artery 102 can easily slip over the leading end 208 of the dilator 203. Both the dilator and sheath may be lubricious to ease insertion into the vessel. As a result of such insertion, the artery 102 expands to an expanded size surrounding the sheath body 215.

With the sheath 201 and dilator 203 fully inserted into the artery 102, the dilator 203 can be removed. The implant leading end 22 is then placed in the sheath body 215. Specifically, the implant leading end 22 is inserted into the guide funnel 207. The guide funnel 207 directs the implant leading end 22 into the cylindrical sheath body 215. So inserted, the leading end 22 of the implant 10 is inserted into the artery 102 and the sheath body 215 is positioned between the implant 10 and the artery 102 protecting the artery 102 from trauma.

After placement of the implant 10, the sheath 201 can be removed. The physician simply pulls on handle 205. This imparts a force which splits the score line 219. With the score line 219 split, the surgeon can pull the sheath body 215 rearwardly out of the vessel 102. The flexible material of the sheath body 215 spreads apart at the bend of the implant 10 to pass the split sheath body 215 over the bend so that the sheath body 215 can be removed without disrupting the position of the artery 102 over the implant's leading end 22. Instead, any frictional force between the artery 102 and the sheath body 215 will tend to further urge the artery 102 over the leading end 22. Therefore, the artery 102 remains over the leading end 22 of the implant 10 and surrounding groove 13 so the artery 102 can be fixed to the implant 10 with sutures 70 (FIG. 2) surrounding groove 13.

Having disclosed the present invention in a preferred embodiment, it will be appreciated that modifications and equivalents may occur to one of ordinary skill in the art having the benefits of the teachings of the present invention. It is intended that such modifications shall be included within the scope of the claims appended hereto.

What is claimed is:

1. A tool for facilitating insertion of a vessel end of a transmyocardial implant into a coronary vessel, said transmyocardial implant having a hollow conduit for establishing a blood flow path through a heart wall between a heart chamber and a lumen of a coronary vessel residing on said heart wall, said vessel end having an external geometry for said vessel end to be received within said lumen, and said vessel end having a generally tubular external geometry and an axial opening at a leading end, said coronary vessel having constricted size and expandable to a larger expanded size, said insertion tip comprising:

a sheath having an internal volume sized to receive said leading end of said implant, and sheath having an external dimension sized for said sheath to be received within said lumen of said expanded size of said coronary vessel, wherein said sheath includes a score at least partially through a thickness of said sheath and extending an partial axial length of said sheath;

a dilator sized to be received within said internal volume and having a dilator leading end sized to be received within said lumen of said constricted size of said coronary vessel; and wherein said dilator includes a generally cylindrical body portion sized to be snugly received within the internal volume of said sheath and said dilator leading end is a taper from the cylindrical portion to a leading tip of said dilator.

2. A tool for facilitating insertion of a vessel end of a transmyocardial implant into a coronary vessel, said transmyocardial implant having a hollow conduit for establishing a blood flow path through a heart wall between a heart chamber and a lumen of a coronary vessel residing on said heart wall, said vessel end having an external geometry for said vessel end to be received within said lumen, and said vessel end having a generally tubular external geometry and an axial opening at a leading end, said coronary vessel having constricted size and expandable to a larger expanded size, said insertion tip comprising:

a sheath having an internal volume sized to receive said leading end of said implant, and sheath having an external dimension sized for said sheath to be received within said lumen of said expanded size of said coronary vessel;

a dilator sized to be received within said internal volume and having a dilator leading end sized to be received within said lumen of said constricted size of said coronary vessel; and wherein said sheath includes a score at least partially through a thickness of said sheath and extending an axial length of said sheath.

3. A tool according to claim 1 where said score is formed completely through a wall-thickness of said sheath.

4. A tool for facilitating insertion of a vessel end of a transmyocardial implant into a coronary vessel, said transmyocardial implant having a hollow conduit for establishing a blood flow path through a heart wall between a heart chamber and a lumen of a coronary vessel residing on said heart wall, said vessel end having an external geometry for said vessel end to be received within said lumen, and said vessel end having a generally tubular external geometry and an axial opening at a leading end, said coronary vessel having constricted size and expandable to a larger expanded size, said insertion tip comprising:

a sheath having an internal volume sized to receive said leading end of said implant, and sheath having an external dimension sized for said sheath to be received within said lumen of said expanded size of said coronary vessel;

a dilator sized to be received within said internal volume and having a dilator leading end sized to be received within said lumen of said constricted size of said coronary vessel; and wherein said sheath includes a guide funnel on a trailing end of said sheath.

* * * * *